(12) United States Patent
Schiedner et al.

(10) Patent No.: US 8,936,908 B2
(45) Date of Patent: Jan. 20, 2015

(54) METHOD FOR THE PRODUCTION OF PERMANENT HUMAN CELL LINES

(75) Inventors: Gudrun Schiedner, Köln (DE); Christoph Volpers, Wiesbaden (DE)

(73) Assignee: CEVEC Pharmaceuticals GmbH, Köln (DE)

( * ) Notice: Subject to any disclaimer, the term of this patent is extended or adjusted under 35 U.S.C. 154(b) by 1765 days.

(21) Appl. No.: 11/370,243

(22) Filed: Mar. 7, 2006

(65) Prior Publication Data

US 2007/0111312 A1 May 17, 2007

(30) Foreign Application Priority Data

Nov. 16, 2005 (DE) .......................... 10 2005 054 628

(51) Int. Cl.
*C12Q 1/68* (2006.01)
*C12N 5/0797* (2010.01)
*C12N 5/073* (2010.01)

(52) U.S. Cl.
CPC ............ *C12N 5/0623* (2013.01); *C12N 5/0605* (2013.01); *C12N 2510/04* (2013.01); *C12N 2799/022* (2013.01); *C12N 2799/06* (2013.01)
USPC ............ 435/6.1; 435/465; 435/467; 435/368

(58) Field of Classification Search
None
See application file for complete search history.

(56) References Cited

U.S. PATENT DOCUMENTS

| | | | | |
|---|---|---|---|---|
| 6,558,948 | B1 * | 5/2003 | Kochanek et al. | 435/325 |
| 6,797,495 | B2 * | 9/2004 | Prusiner | 435/70.21 |
| 6,855,544 | B1 * | 2/2005 | Hateboer et al. | 435/325 |
| 2003/0185801 | A1 * | 10/2003 | Vogels et al. | 424/93.2 |

FOREIGN PATENT DOCUMENTS

| | | |
|---|---|---|
| JP | 2003-514526 | 4/2003 |
| JP | 2002-541854 | 12/2010 |
| WO | WO 02/40665 | 5/2002 |
| WO | WO 2004/009618 A2 * | 1/2004 |
| WO | WO 2004/099396 | 11/2004 |

OTHER PUBLICATIONS

Kim and Lee, "Cytogenetic analysis of chimeric antibody-producing CHO cells in the course of dihydrofolate reductase-mediated gene amplification and their stability in the absence of selective pressure," *Biotechnol. Bioeng.*, 64:741-749, 1999.
Louis et al , "Cloning and Sequencing of the Cellular-Viral Junctions from the Human Adenovirus Type 5 Transformed 293 Cell Line," *Virology*, 233:423-429, 1997.
Ludlow, "Interactions between SV40 large-tumor antigen and the growth suppressor proteins pRB and p53," *FASEB J.*, 7:866-871, 1993.
Moran, "Interaction of adenoviral proteins with pRB and p53," *FASEB J.*, 7:880-885, 1993.
Wurm et al., "Integration and stability of CHO amplicons containing plasmid sequences," *Dev. Biol. Stand.*, 76:69-82, 1992.
Wurm, "Production of recombinant protein therapeutics in cultivated mammalian cells," *Nat. Biotechnology*, 22:1393-1398, 2004.
Zur Hausen, "Papillomaviruses causing cancer: evasion from host-cell control in early events in carcinogenesis," *J. Natl. Cancer Inst.*, 92:690-698, 2000.
Huang et al., "Enhancing protein expression in singlel HEK 293 cells," *Journal of Neuroscience Methods*, 142( 1):159-166, 2005.
Janahi et al., "Establishment of human microglial cell lines after transfection of primary cultures of embryonic microglial cells with the SV40 large T antigen," *Neuroscience Letters*, 195:105-108, 1995.
Jenkins et al., "SV40-transformed fragile (X) amniocytes," *American Journal of Medical Genetics*, 38:464-466, 1991.
Jenkins et al., "Transformation and establishment of fragile X cell lines from amniocytes." *American Journal of Medical Genetics*, 38:416-417, 1991.
Jones et al., "PER.C6 cell line for human antibody production," *Genetic Engineering News*, 22(10):50, 54, 2002.
May et al.,"Application of a reversible immortalization system for the generation of proliferation-controlled cell lines," *Cytotechnology*, 46:69-78, 2004.
Office Communication issued in Chinese Patent Application No. 200680043000.3, dated Sep. 20, 2010. (English translation).
Office Communication issued in Japanese Patent Application No. 2008-540447, dated Jan. 5, 2012. (English translation).
PCT International Preliminary Report on Patentability issued in International application No. PCT/DE2006/002004, dated Jul. 8, 2008. (English translation).
PCT International Search Report issued in International application No. PCT/DE2006/002004, dated Aug. 21, 2007. (English translation).
Schiedner et al., "Efficient transformation of primary human aminocytes by E1 functions of Ad5: Generation of new cell lines for adenoviral vector production," *Human Gene Therapy*, 11(15):2105-2116, 2000.
Tahara and Ide, "5. Cell Immortalization," In: Experimental Cultivation of Cells Handbook. Experimental Medicine Additional Volume. Chapter 4: Cell Reproduction and Death. Toshio Kuroki and Nanbo Ho, Eds., Tokyo: Yodosha Co., Ltd., 2004. (English translation of Japanese publication).
Walen and Arnstein, "Induction of tumorigenesis and chromosomal abnormalities in human aminocytes infected with simian virus 40 and Kirsten Sarcoma virus," In Vitro *Cellular and Developmental Biology*, 22(2):57-65, 1986.
Walen, "Chromosome instability in cell lineages of aniniocyte clones morphologically transformed by simian virus 40," *Cancer Genet. Cytogenet.*, 25:149-159, 1987.

\* cited by examiner

*Primary Examiner* — Jim Ketter
(74) *Attorney, Agent, or Firm* — Parker Highlander PLLC

(57) ABSTRACT

The present invention relates to a method for the production of a permanent human cell line, wherein isolated primary human cells are transfected simultaneously with a sequence allowing the expression of at least one cell transforming factor and a sequence allowing the expression of at least one recombinant polypeptide.

11 Claims, 6 Drawing Sheets

METHOD FOR THE PRODUCTION OF PERMANENT HUMAN CELL LINES

The present invention relates to a method for the production of a permanent human cell line, wherein isolated primary human cells are transfected simultaneously with a sequence allowing the expression of at least one cell transforming factor and a sequence allowing the expression of at least one recombinant polypeptide.

The production of recombinant polypeptides for therapeutic, diagnostic or technical purposes in cell culture (in vitro) is in general carried out in stable, durably or permanently established cell lines in which the nucleic acid encoding the polypeptide is integrated into the chromosomal DNA of the cell (so-called production cell line). These production cell lines have to exhibit in particular two characteristic properties: firstly, they have to grow durably (permanently) in cell culture and be propagatable, and, secondly, they have to express the gene encoding the desired polypeptide that, subsequently, can be isolated from the cell or from the supernatant of the culture. Besides bacteria, yeasts and plant cells, animal cells are used, in particular, for the production of recombinant polypeptides. About 60-70% of all therapeutic proteins are nowadays produced in mammalian cells (Wurm, Nat. Biotechnology 22, 1393-1398, 2004). The production of the production cells usually starts from already immortalised or transformed cell lines that grow permanently in cell culture and propagate, such as animal derived CHO (Chinese Hamster Ovary), BHK (Baby Hamster Kidney), NSO (Mouse Myeloma) cells or human HEK293 (Human Embryonic Kidney) or PER.C6 cells. These cell lines, which have become commercially available in the meantime, were generated from primary cells in culture virtually as a first step of the method for establishing production cells by genetic manipulations, or isolated from a natural tumour.

In the case of the generation of the actual production cells, on the one hand, the nucleic acid encoding the recombinant polypeptide (the so-called transgene) together with the necessary transcriptional regulatory elements is transferred into these already established cell lines by transfection, and on the other hand, a second expression cassette with a gene encoding a selection marker and whose gene product provides the cell with a certain selectional advantage is transferred. A few days after the gene transfer, during which the cells were cultivated in a culture medium without selection reagent, the medium is provided with a suitable selection reagent. In presence of the selection reagent only those cells survive and grow which took up the nucleic acids used for the transfection and which express the selection marker. Selection markers that are frequently used are the neomycin resistance gene, the hygromycin resistance gene and the dihydrofolate reductase (DHFR) (Wurm, Nat. Biotechnology 22:1393-1398, 2004; Wurm and Jordan, 309-333 in: Makrides (Eds.), Gene Transfer and Expression in Mammalian Cells, Elsevier, Amsterdam, 2003). The selection is performed accordingly in culture medium with the selection reagents, such as the antibiotics neomycin or hygromycin, and with the synthetic glucocorticoid methotrexate, respectively. Cells having the selection marker and the transgene, which survive the selection process and proliferate (so-called transformants), are usually subsequently individualised (cloned) to make sure that all cells in the culture are genetically identical and in order to separate the desired production cell lines having the best production rate from the less well producing cell lines.

The selection reagents have to be added into the medium, depending on the production process, possibly not only during the selection phase but also later during the growth of the cloned cells, in order to guarantee the genetic stability of the production cell lines. The gene for the desired polypeptide (transgene) and the gene for the selection marker integrate usually within the same site of the cellular genome. If there is no selectional pressure during the later expansion of the cells, or during the production phase, the danger arises that the cells lose the selection marker—and with it also the transgene for the desired polypeptide. This is prevented by the continuous addition of the selection reagent.

Primary animal and human cells that are taken into cell culture after removal from the organism or tissue usually grow only a short period of time and over few passages. Human cells are especially suited for the production of human biotherapeutics since they express complex polypeptides—in contrast to other mammalian or animal cells—with authentic post-translational modification pattern. The glycosylation pattern of complex recombinant proteins, i.e., the structure and configuration of the sugar residues within the molecule will, in case of a production of human cells, reproduce considerably better the pattern of the authentic human polypeptide than in case of a production in non-human production systems. This glycosylation pattern is frequently of decisive importance for important properties of the polypeptide such as biological activity, stability, solubility and immunogenicity.

Durably established human cell lines (permanent human cell lines), which can be used for the expression of recombinant polypeptides, were isolated from tumour tissue of patients (e.g., HeLa cells). However, such cells are not suited for an industrial production of therapeutical polypeptides to be applied to humans because of security relevant considerations and because of their genetic instability. Besides very few exceptions (e.g., the so-called HaCaT cells), spontaneously immortalised human cell lines are practically not available. In contrast, permanent human cell lines generated by transformation of primary tissue by certain viral gene products are suitable for biotechnological production purposes. By expression of transforming polypeptides of DNA viruses, primary cells can be transferred into permanently growing cells. The mechanism of transformation requires the interaction of the virus encoded gene products with cellular proteins that play a role in the regulation of the cell division (so-called tumour suppressor gene products). Thereby, an arrest of the cell cycle (G0/G1 phase) is interrupted and the cells enter the S phase leading to an uncontrolled proliferation of the cells (Helt & Falloway, Carcinogenesis 24:159-169, 2003). Examples for such transforming, virus encoded gene products are the T-antigen of the Simian Virus 40 (SV40), E6/E7 of the human papilloma virus (HPV) or E1A/E1B of adenovirus. These viral proteins are comparable in their mechanism of transformation: T-antigen, E6 and E1A inactivate gene products of the cellular retinoblastoma protein family (pRb), and T-antigen, E7 and E1B inactivate the cellular tumour suppressor p53 (reviewed in: zur Hausen, J. Natl. Cancer Inst, 92, 690-698, 2000; Ludlow, FASEB J. 7: 866-871, 1993; Moran, FASEB J. 7, 880-885, 1993). The cell lines transformed in such a way become permanently cultivable and are especially suited for biotechnological production purposes.

Only very few human cell types have been transformed by the adenoviral E1 gene region by now. Amongst them, there are neuronal cells of human embryonic kidney tissue (HEK293) (Graham et al., J. Gen. Virol. 36:59-74, 1977), human embryonic retina cells (EP 833 934 B1) und human amniocytes (EP 1 230 354 B1).

The described method for the production of production cell lines based on available immortalised and transformed, respectively, cell lines brings about drawbacks in different respects. The addition of antibiotics, chemotherapeutics or other selection reagents to the culture medium during the selection phase, and possibly also during the expansion phase, prior to the production increases the costs for the production method. Besides that it must be secured and confirmed by laborious analyses during the production process as well as by analysis of the end product that the purified and confectioned end product does not retain any residual selection reagents. This means additional requirements for the quality control to ensure the security of the therapeutic preparation. Some of the applied selection reagents display, in addition, an influence on the quality and clonal stability, respectively, of the production cell. The continuous addition of methotrexate as a selection reagent to the culture, for example, maintains, in the case of some production cell lines, the impression of a "stable" phenotype of the cell in regard to its productivity. However, genetic analyses have shown that the presence of this reagent enhances the cytogenetic heterogeneity of the cells which is not desired, in particular in respect to the regulatory requirements of the process of accreditation (Wurm et al., Dev. Biol. Stand. 76:69-82, 1992; Kim and Lee, Biotechnol. Bioeng. 64:741-749, 1999). A further disadvantage of the classical method for the generation of production cell lines can be seen in the fact that there is only a very limited selection of permanent starting cell lines available on which the method of production is based (e.g., CHO, BHK, HEK293). All these cells have been cultivated over countless passages over the years and stored prior to their development to production cell lines. These actions always harbour the risk to accumulate, in addition to the genetic changes necessary for the initial immortalisation, further chromosomal aberrations and genetic mutations that render them more and more unlike the "natural" animal and human, respectively, starting cell. Possible consequences of these changes for security relevant and/or production technical aspects of the genetic engineering of recombinant proteins have not been analysed in detail up to now.

Thus, the problem underlying the present invention is to provide a more simple, more cost-effective and, under toxicity aspects, safer method for the production of permanent human cell lines for the production of recombinant polypeptides.

The problem is solved by the subject-matter defined in the patent claims.

The following figures illustrate the invention.

Figure 4:
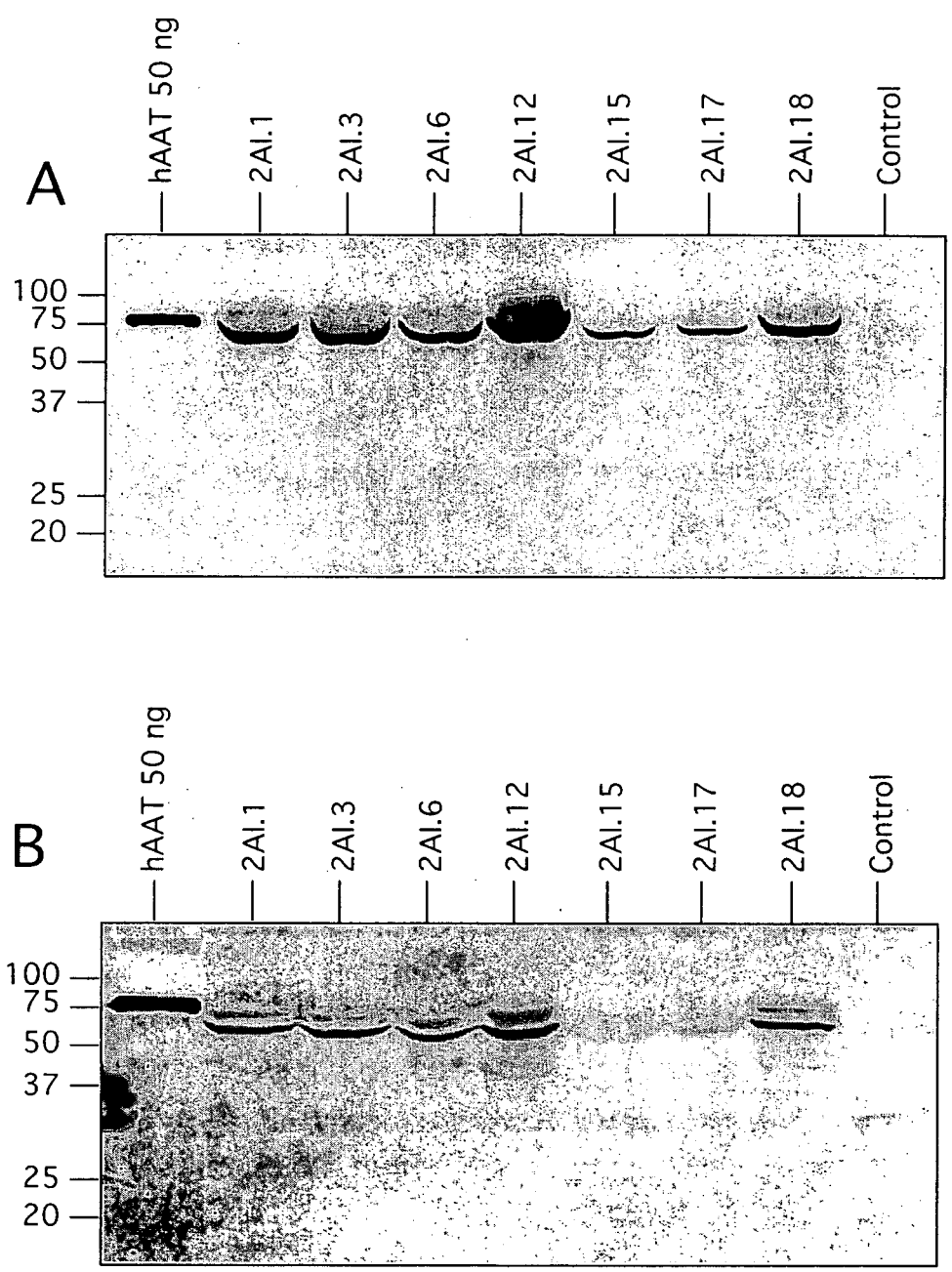

FIG. 4 shows the result of a Western blot in respect to the expression of human alpha 1-antitrypsin (hAAT) in seven different permanent amniocyte based production cell lines. A, hAAT secreted from the cells into the culture supernatant; B, intracellular hAAT.

Figure 5:
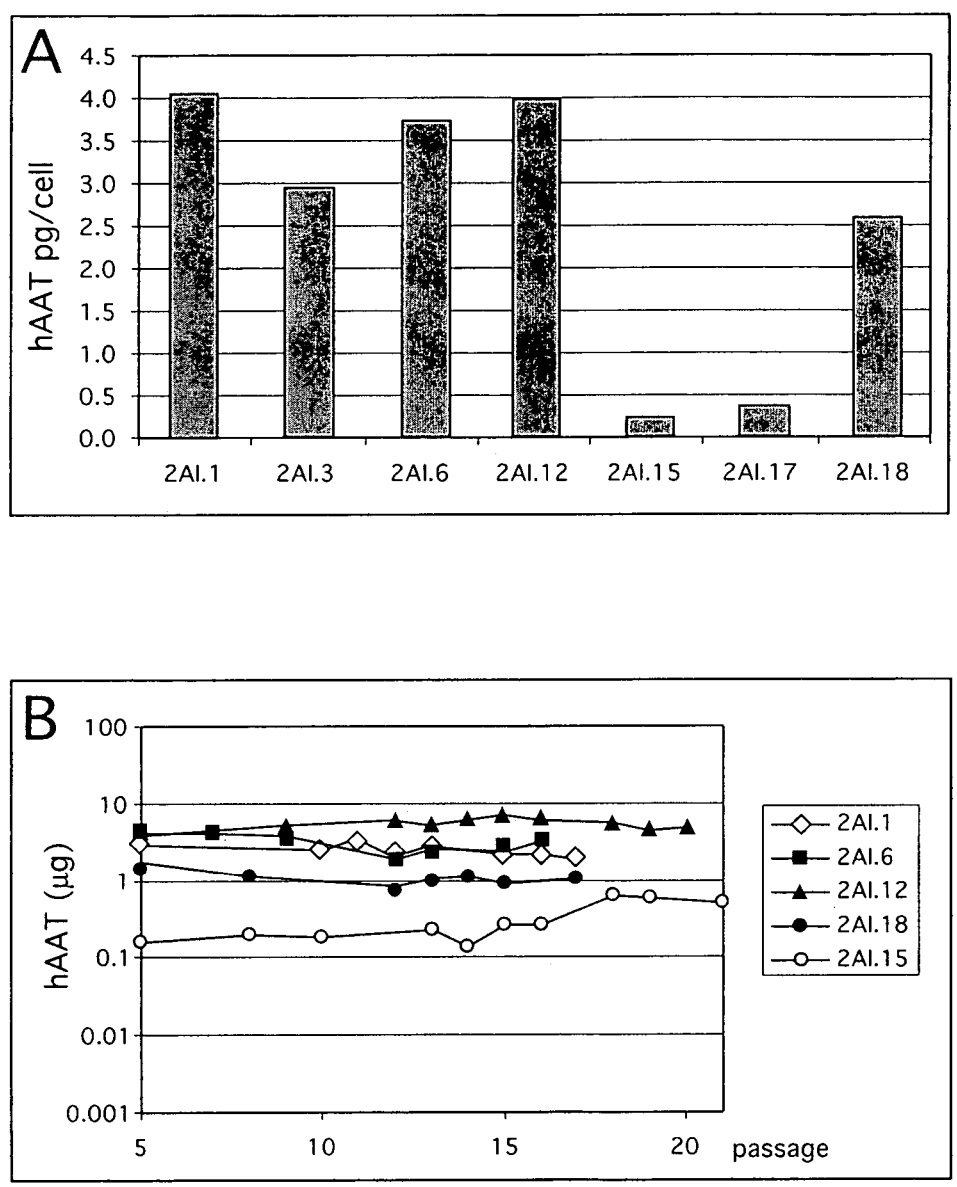

FIG. 5 shows schematically the amount of human alpha 1-antitrypsin (hAAT) expressed by selected production cell lines in the culture supernatant (ELISA, Enzyme-linked Immunosorbent Assay). A, amount of hAAT in passage 5 of the individual cell clones; B, stability of expression over several passages in selected cell clones.

Figure 6:
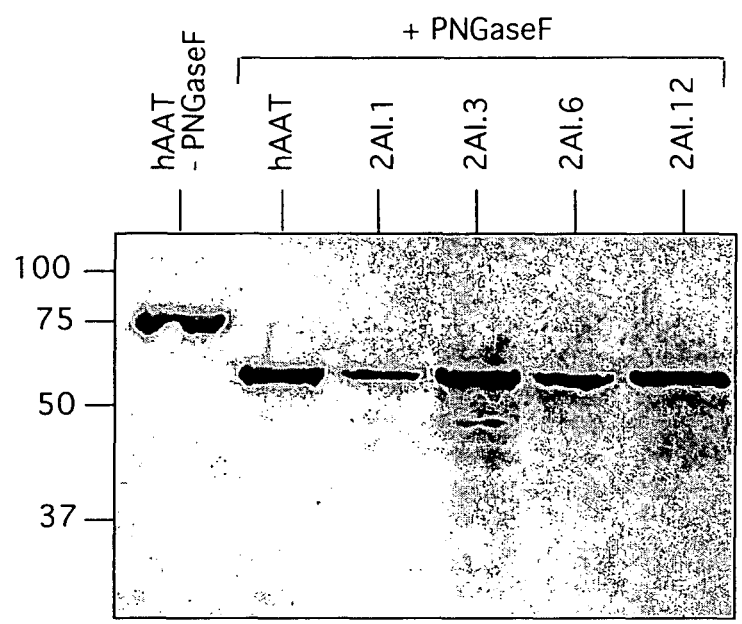

FIG. 6 shows the result of a Western Blot in respect to the glycosylation of human alpha 1-antitrypsin (hAAT) from amniocyte based production cell lines.

The term "amniocyte", as used herein, relates in the broadest sense to all cells that are present in amniotic liquor and may be obtained by amniocentesis. They originate either from amnion or from foetal tissue that is in contact with the amniotic liquor. Three main classes of amniocytes have been described that can be distinguished based on morphological criteria: fibroblast like cells (F cells), epitheloid cells (E cells) and amniotic fluid cells (AF cells), (Hohn et al., Pediat. Res. 8:746-754, 1974). AF cells are the predominant cell type.

The term "expression cassette" relates particularly to a nucleic acid molecule and a region of a nucleic acid molecule, respectively, containing a regulatory element or promoter being positioned in front of the coding region, a coding region and an open reading frame, respectively, as well as a transcriptional termination element lying behind the coding region. The regulatory element and the promoter, respectively, residing in front of the coding region, can be a constitutive, i.e., a promoter permanently activating the transcription (e.g., CMV promoter), or a regulatable promoter, i.e., a promoter which can be switched on and/or off (e.g., a tetracycline regulatable promoter). The coding region of the expression cassette can be a continuous open reading frame as in the case of a cDNA having a start codon at the 5' end and a stop codon at the 3' end. The coding region can be comprised of a genomic or a newly combined arrangement of coding exons and interspersed non-coding introns. However, the coding region of the expression cassette can be comprised of several open reading frames, separated by so-called IREs (Internal Ribosome Entry Sites).

The term "permanent cell lines", as used herein, relates to cells which are genetically modified in such a way that they may continue to grow permanently in cell culture under suitable culture conditions. Such cells are also called immortalised cells.

The term "polypeptide" or "recombinant polypeptide", as used herein, relates to peptides consisting of at least 2 amino acids. The polypeptide can be modified co- and/or post-translationally, e.g., by the attachment of sugar residues or by modification of amino acid residues. The polypeptide can be linear, circular or branched. Furthermore, the polypeptide can consist of more than one amino acid chain, wherein the chains may adopt more or less complex three-dimensional structures by intra- and/or intermolecular bonds (e.g., secondary, tertiary, quaternary structure). If the polypeptide consists of one amino acid chain it can adopt more or less complex three-dimensional structures also by intramolecular bonds. The polypeptides can be pharmacologically or immunologically active polypeptides or polypeptides used for diagnostic purposes.

The term "primary cells", as used herein, relates to cells that were obtained by direct removal from an organism or a tissue and put in culture. Primary cells exhibit only a very limited life span.

The term "production cell lines", as used herein, relates to permanent cell lines that were genetically modified by the introduction of a transgene encoding the desired polypeptide to be produced.

The term "transfection", as used herein, relates to any method suitable for the introduction of the mentioned nucleic acid(s) into the cells. As examples the classical calcium phosphate method, electroporation, liposomal systems of any kind and combinations of these methods are to be mentioned.

The term "transgene", as used herein, relates to a nucleic acid sequence encoding a recombinant polypeptide.

An aspect of the present invention relates to a method for the production of a permanent human cell line, wherein isolated primary human cells are transfected by a nucleic acid molecule or at least two different nucleic acid molecules, and in case that one nucleic acid molecule is transfected, the nucleic acid molecule exhibits a sequence allowing the expression of at least one cell transforming factor and the expression of a recombinant polypeptide, and in case that at least two different nucleic acid molecules are transfected, a first nucleic acid molecule exhibits a sequence allowing the expression of at least one cell transforming factor, and a second nucleic acid molecule exhibits a sequence allowing the expression of at least one recombinant polypeptide.

The primary human cells used for the method of the present invention are obtained by direct removal from the organism or a tissue removed from the organism and put in culture. Preferred are such primary human cells, which can be well turned into permanent human cell lines by expression of cell transforming factors, in particular amniocytes, embryonic retina cells as well as embryonic cells of neuronal origin.

Cell transforming factors may be the T-antigen of SV40 (GeneBank Acc. No. J02400), the E6 and E7 gene products of HPV (e.g., HPV16, GeneBank Acc. No. K02718) and the E1A and E1B gene products of human adenoviruses (e.g., human adenovirus serotype 5, GeneBank Acc. No. X02996). If nucleic acid sequences for the E6 and E7 gene products are used for the method according to the invention, the primary human cells have to be transfected by the sequences for both gene products. If the nucleic acid sequences for the E1A and E1B gene products are used for the method according to the invention, the primary human cells have to be transfected by the sequences for both gene products. In case of the expression by a naturally occurring HPV, E6 and E7 can be expressed from an RNA transcript. The same applies for the expression of E1A and E1B of an adenovirus which is naturally occurring. The cell transforming factors such as the adenovirus E1 gene function effect the immortalisation or transformation of the cells and therefore their ability to be durably cultivated. Non-transfected primary human cells die naturally within the culture at least after a few weeks, whereas the transfected cells proliferate to phenotypically recognisable cell colonies because of the immortalising activity of e.g. the E1 gene products. The transfer of the cell transforming factors, which transfer is essential for the immortalisation of the cells, thus takes over the function of a selection marker within the method according to the invention which selection marker allows the isolation of cell lines without any additional exogenous chemical selection pressure, wherein the cell lines express one or more different recombinant polypeptides.

The nucleic acid sequences for the expression of the cell transforming factors are present in form of an expression cassette.

The expression cassettes may contain homologous promoters and transcriptional termination sequences, respectively, e.g., the natural E1A promoter and the natural E1A polyadenylation site for the expression of the adenoviral E1A gene function. This can be achieved if the nucleic acid molecules used for the transfection contain fragments of the respective viral genome, e.g. of the adenoviral genome exhibiting the said gene functions, e.g., E1A, E1B. The expression cassettes for the cell transforming factors may also contain heterologous promoters that do not occur naturally with the coding region used or transcriptional termination sequences. As heterologous promoters can serve e.g.: CMV (cytomegalovirus) promoter (Makrides, 9-26 in: Makrides (Eds.), Gene Transfer and Expression in Mammalian Cells, Elsevier, Amsterdam, 2003), EF-1α promoter (Kim et al., Gene 91:217-223, 1990), CAG promoter (a hybrid promoter from the immediate early enhancer of the human cytomegalovirus and a modified chicken P-actin promoter with the first intron) (Niwa et al., Gene 108:193-199, 1991), human or murine pgk (phosphoglycerate kinase) promoter (Adra et al., Gene 60:65-74, 1987), RSV (Rous Sarcoma Virus) promoter (Makrides, 9-26 in: Makrides (Eds.), Gene Transfer and Expression in Mammalian Cells, Elsevier, Amsterdam, 2003) or SV40 (Simian Virus 40) promoter (Makrides, 9-26 in: Makrides (Eds.), Gene Transfer and Expression in Mammalian Cells, Elsevier, Amsterdam, 2003). As polyadenylation sites may serve e.g. the polyadenylation sequences of the SV40 large T-antigen (GeneBank Acc. No. J02400) or of the human G-CSF (granulocyte colony stimulating factor) gene (Mizushima and Nagata, Nucl. Acids Res. 18:5322, 1990). Likewise, some of the expression cassettes may contain homologous regulatory elements and other heterologous regulatory elements for the transforming factors. That is, the E1A expression cassette may, e.g., exhibit a heterologous promoter, the E1B expression cassette may exhibit a homologous promoter or vice versa, or both expression cassettes exhibit a heterologous promoter.

The nucleic acid sequences for the expression of the at least one recombinant polypeptide are present in at least one expression cassette, too, wherein the kind and the selection of the promoters and of the transcriptional termination sequences correspond to those mentioned for the cell transforming factors.

The nucleic acid sequences of the cell transforming factors and of the recombinant polypeptide including the respective regulatory elements may be present on one or several different nucleic acid molecules. In a preferred embodiment of the present invention the sequences of the cell transforming factors including the respective regulatory elements, e.g., the E6 and E7 gene functions or the E1A and E1B gene functions, or the cell transforming factor, e.g., the T-antigen of SV40, are present on a nucleic acid molecule and the sequences of the recombinant polypeptide including the regulatory elements are present on a second nucleic acid molecule which is distinct from the first nucleic acid molecule. In a further preferred embodiment also the sequences of the transforming factors E6 and E7, and E1A and E1B, respectively, including the respective regulatory elements are present on different nucleic acid molecules. The sequence of the recombinant polypeptide including the regulatory elements can, in this case, be present on a third nucleic acid molecule, which is distinct from the first and second nucleic acid molecule, or on the first or second molecule, comprising the sequence for one of the cell transforming factors. In a preferred embodiment the primary human cells are transfected by a first nucleic acid molecule containing the expression cassette of the E1A and E1B gene functions and a second nucleic acid molecule exhibiting the expression cassette of the recombinant peptide, which second nucleic acid molecule is distinct from the first nucleic acid molecule. In this embodiment the first nucleic acid molecule contains the E1A expression cassette containing a heterologous promoter and the homologous transcriptional termination element, and the E1 B transcriptional unit contains the homologous promoter and the homologous transcriptional termination element. In an especially preferred embodiment the first nucleic acid molecule contains the adenovirus serotype 5 nucleotide sequence from nucleotide 505 to nucleotide 4079. In a further especially preferred embodiment the first nucleic acid molecule contains the adenovirus serotype 5 nucleotide sequence from nucleotide 505 to nucleotide 3522. In a further especially preferred embodiment the first nucleic acid molecule contains the adenovirus serotype 5 nucleotide sequence from nucleotide 1 to nucleotide 4344 corresponding to the adenoviral DNA in HEK293 cells (Louis et al., Virology 233:423-429, 1997).

The presence of the E1B promoter and the E1B polyadenylation sequence (nucl. 4037-4070) should lead to an optimal transcription and expression of E1B in the case of this embodiment. A further advantage resides in the fact that the sequence region between the stop codon of E1B and the polyadenylation site of E1B contains the adenoviral pIX gene function. The pIX polypeptide, a viral structural protein, acts as a transcriptional activator on different viral and cellular promoters such as the thymidine kinase and the beta globin promoter. The transcriptional activating effect of the pIX polypeptide which is in addition expressed in the cell can lead to an increase of the expression rates of the recombinant polypeptide within the production cell lines according to the invention if the coding sequence of the recombinant polypeptide is under the control of one of the promoters mentioned above.

The recombinant polypeptides may be therapeutic proteins such as the human alpha 1 antitrypsin or growth factors such as erythropoietin or interleukin-2. Human alpha 1-antitrypsin (hAAT) is a proteinase inhibitor which inhibits elastase and other proteinases and which is therapeutically active in the case of inherited hAAT deficiency leading to severe damages of the lung and the liver. Erythropoietin is an important growth factor for erythrocytes (red blood cells) that has a blood forming activity in the case of anaemia as well as in the case of transplantation patients. Interleukin-2 (I1-2) is a cellular messenger of the immune system and is of significant importance in the case of the activation of the cellular immune response, for example in the case of tumour diseases. Blood clotting factors, such as factor VIII and IX used in the case of haemophilia patients having blood clotting disorders, also belong to the therapeutically active polypeptides. The recombinant polypeptide according to the method according to the invention may be a hormone. Biotechnologically engineered hormones are used in the substitution therapy in the case of patients having hormonal disorders. Examples are the blood sugar lowering hormone insulin, upon which many patients having diabetes mellitus are dependent, somatotropin (growth hormone) for the treatment of dwarfism, and gonadotrope factors such as the follicle stimulating hormone (FSH) or luteinising hormone (LH) for the treatment of fertility disorders.

The recombinant polypeptide can be a recombinant antibody which may be used for therapeutic or diagnostic purposes. Antibodies against the tumour necrosis factor alpha (TNF-α) are used in the case of patients with rheumatoid arthritis, antibodies against the cellular receptor of the epidermal growth factor (EGFR) are used in the case of cancer patients. Antibodies used for diagnostic purposes may be for example components of commercial diagnosis kits based on methods such as the enzyme-linked immunosorbent assay (ELISA) or the radio immunosorbent assay (RIA). In these test assays, the antibodies serve for the detection of the antigens of infectious agents such as the human hepatitis B virus.

Antibodies or immunoglobulines (Ig) consist of a heavy and a light chain each consisting of variable and constant regions or domains. The nucleic acid sequences of the transfected nucleic acid molecules for the expression of an antibody may contain two separated expression cassettes, one of which encoding the light chain and the other the heavy chain of the immunoglobuline molecule. Upon expression of both chains in the cell according to the invention these chains assemble to form the active antibody molecule. The expression cassettes of the two chains may be present on separated or on the same nucleic acid molecule(s). The coding sequences for the light and heavy chain may, however, be present within the same expression cassette and be separated by an IRES sequence (internal ribosome entry site) providing for an expression of both the heavy and the light chain. The coding sequences for the light and the heavy chain may in principle also be present within the same expression cassette and be separated by a sequence encoding an enzymatic cleavage site for a proteinase (e.g., thrombin) which is simultaneously expressed within the cell and which cleaves the precursor polypeptide consisting of the sequence of the light and heavy chain into the active light and heavy chain.

Recombinant antibodies encoded by the nucleic acid sequence of the cell according to the invention may also consist of fragments of an antibody instead of the complete light and heavy chain. So-called single chain antibodies (scFv, single chain variable fragments) consist of the variable domains of a heavy and a light chain linked by an amino acid sequence (a so-called linker) providing for a free motility of both domains. An antigen binding structure is formed by the intramolecular assembly of both domains, which structure corresponds to the variable region of an immunoglobuline molecule. Bispecific single chain antibodies (bis-scFv) consist of two of such single chain assemblies made up of the variable domains of a heavy and a light chain which in turn are linked by a connecting sequence and are motile against each other; such molecules may simultaneously bind to two antigen binding sites (epitopes) thereby connecting two molecular structures in a non-covalent manner. Bispecific diabodies consist of two single chains which are expressed separately and each of which consist of variable domains of a light and a heavy chain each, separated only by a very short linker or they are without a linker at all. The short or lacking linker inhibits the intra molecular assembly; by intramolecular assembly of a variable heavy and light domain an active molecule having two binding valences is formed once more.

The recombinant polypeptides encoded by the nucleic acid molecules transfected in the present method may be viral, bacterial or parasitic proteins which are to be produced for a use as prophylactic or therapeutic vaccines. These proteins may be both structural polypeptides and regulatory or enzymatically active polypeptides from viruses, bacteria or parasites. Viral proteins may be, e.g., the hepatitis B virus surface antigen (HBV surface antigen) or the structural protein L1 from human papilloma viruses. Bacterial proteins which are considered for the production of vaccines after the expression in production cell lines are, e.g., enterotoxine subunits from enterotoxinogeneous *Escherichia coli* (ETEC) or transferrin binding proteins (Tbp A and B) from *Neisseria gonorrhoeae*. Polypeptides from parasites, which polypeptides may be encoded by the nucleic acid molecules transfected in the present method are, e.g., the merozoite surface protein (MSP) of the causative agent of malaria *Plasmodium falciparum* or glutathione S transferase (GST) from *Schistosoma japonicum*.

The recombinant polypeptides encoded by the nucleic acid molecules transfected in the present method may be one or more viral polypeptide(s) which is/are active as replication factor(s) and which allow an episomal, i.e. a chromosome independent, replication of nucleic acid molecules subsequently introduced into the cell line by transfection within the human cell line. The nucleic acid molecules subsequently introduced into the cell line by transfection contain a genetic element denoted "origin of replication" (ori), to which element the polypeptide(s) acting as replication factor(s) bind(s), thereby initiating the replication of the episomal nucleic acid molecule. The episomal replication of nucleic acid molecules, in particular of plasmid DNA, in cells effects a strong increase of the copy number of the transferred nucleic acid molecules thereby increasing the expression of a recombinant polypeptide encoded by this molecule as well as its maintenance during many cell divisions. Such a viral replication factor is, e.g., the T-antigen of the Simian virus 40 (SV40) which, upon binding to a sequence denoted as a SV40 origin of replication (SV40 ori) on the nucleic acid molecule, e.g., the plasmid DNA, initiates its replication. The Epstein-Barr virus protein EBNA-1 (Epstein-Barr Virus Nuclear Antigen-1) recognises an origin of replication denoted as ori-P and catalyses the extrachromosomal replication of the ori-P carrying nucleic acid molecule.

The recombinant polypeptides encoded by the nucleic acid molecules transfected in the present method can also be viral proteins allowing a production of recombinant viral gene transfer vectors within the cell lines. These viral proteins, also called complementation factors, are expressed within the cell line and are the enzymatic or structural components necessary for the production of the gene transfer vectors, which components are not encoded on the nucleic acid molecule of the gene transfer vector. In such gene transfer vectors certain viral gene functions are usually deleted because of security considerations. Gene transfer vectors, whose complementation factors may be encoded by the transgene introduced by the described method, are for example vectors which are based on adenovirus, adenovirus associated virus (AAV) or herpes virus. The complementation factors expressed within the cell line may also complement deleted or recombinant viruses during their production, which viruses do not contain a gene to be transferred and thereby not acting as a gene transfer vector but are used, e.g., as a vaccine.

In the case of adenovirus based gene transfer vectors, for example the gene functions pIX, E2, E3 and/or E4 may be expressed within the cell according to the invention. The deletion of the respective gene function from the genome of the vector increases the security of the vectors and increases its capacity for the uptake of unrelated nucleic acid sequences. The gene function pIX is an adenoviral structural protein, i.e., a component of the viral capsid. The viral gene functions E2, E3 and E4 encode regulatory polypeptides which are expressed in the early phase of the viral replication. Adenoviral vectors of the first generation are merely deleted for E1 and/or E3. Adenoviral vectors of the second generation lack additionally the gene functions E2 and/or E4. Cell lines complementing all viral gene functions would be, in principal, able to complement the generation of adenoviral gene transfer vectors which are denoted as "gutless" vectors or high capacity adenoviral vectors, which do not contain any coding gene functions any more but have only the sequences for the replication of the vector nucleic acid, said sequences being denoted inverted terminal repeats (ITRs).

The nucleic acid transfected with the present method into the primary human cell may furthermore encode a receptor polypeptide which is in particular localised on the surface of the cell and which is responsible for the infection of the cell by a virus and the transduction of the cell by a viral gene transfer vector, respectively. As a viral receptor for the initial step of infection of cells with the adenovirus serotype 2 or 5, from which the most conventional adenoviral vectors are derived, the so-called Coxsackie and adenovirus receptor, CAR, was identified (Bergelson et al., Science 275:1320-1323, 1997). The sufficient expression of CAR on the surface is a prerequisite that a cell is suitable to be a production cell for adenoviral gene transfer vectors. In a preferred embodiment the recombinant polypeptide is the Coxsackie and adenovirus receptor (CAR). The overexpression of the receptor polypeptide can significantly improve the infectibility and, thus, the production efficiency of these cells in regard to adenoviral vectors. Furthermore the nucleic acid molecule may encode, besides CAR, secondary receptors or internalising receptors such as certain integrins that mediate the uptake of the virus and gene transfer vector, respectively, into the cell and whose additional expression is advantageous in the production of production cells for adenoviral vectors.

The nucleic acid molecules used in the present method for the transfection of primary human cells, which nucleic acid molecules encode the at least one recombinant polypeptide, or the nucleic acid molecules encoding the cell transforming factors may contain "matrix attachment regions" (MARs). These genetic elements, also denoted as "scaffold attachment regions" (SARs), play a role in the regulation of the gene expression since they are associated with transcriptional units and regulatory elements within the genome. MARs are able to protect foreign genes integrated into a cell against a transcriptional muting or shut-off of the transcription within the transfected cell thereby enhancing their expression (Girod and Mermod, p. 359-379, in S. C. Makrides (Eds.) Gene Transfer and Expression in Mammalian Cells. 2003. Elsevier, Amsterdam).

By the simultaneous transfection of primary human cells with nucleic acid molecules containing expressible nucleic acid sequences for a cell transforming factor and two functionally linked factors, respectively, and an expressible nucleic acid sequence of at least one recombinant polypeptide the inventors have succeeded to generate permanent human cell lines for the production of recombinant polypeptides without the addition of selection reagents. Thus, the invention relates furthermore to the permanent human cells generated by the method according to the invention. The cells may be used, inter alia, for the production of therapeutic polypeptides, blood clotting and growth factors, hormones and antibodies as well as viral, bacterial or parasitic polypeptides for use as vaccine. Furthermore, the cells according to the invention may be used for the production of diagnostically relevant proteins such as viral, bacterial or parasitic antigens or respective specific antibodies. Furthermore, the cells according to the invention may be used for the production of technically or industrially relevant proteins such as enzymes for the catalysis of technical synthesis processes or for the degradation of harmful substances. The cells according to the invention may express one or also more different recombinant polypeptides. The number of expressible polypeptides is dependent on how many different nucleic acid sequences encoding the recombinant polypeptides are transfected into the cells with the method according to the invention.

The strength of expression of a transgene in a production cell is crucially dependent on the genomic region in which the transgene integrates after its introduction into the cell. Whereas the expression of the transgene is shut off after a relatively short time at some sites of the cellular genome, the expression cassette remains transcriptionally active with high efficiency over a long time at other sites, the so-called "hot spots" of transcription. The maintenance of the transformed phenotype in the permanent cells produced according to the invention requires a continuous expression of the cell transforming factors. In the permanent human cells, the integration site of the respective expression cassette resides thus at a "hot spot" of transcription within the cellular genome. A further aspect of the present invention relates therefore to a method for the production of a permanent human cell, wherein the nucleic acid molecule exhibiting the sequence for the cell transforming factor(s) further comprises recognition sequences of a sequence specific recombination enzyme. In a subsequent step, a further expression cassette for a transgene may be integrated in the permanent human cell line whereas the respective recombinase is simultaneously expressed, wherein the expression cassette also contains a respective recombinase recognition sequence or recombinase recognition sequences. This leads to an integration of the expression cassette at the specific "hot spot" and thus to a high, long lasting expression of the transgene. Production cell lines having a determined high production efficiency, which cell lines have been generated in the described fashion, could be used in order to rapidly generate efficient production cells for another transgene.

A further aspect of the present invention relates to a method for the production of a permanent human cell line, wherein the nucleic acid molecule exhibiting the sequence allowing the expression of a recombinant polypeptide exhibits, in addition to the expression cassette of the recombinant polypeptide or to the coding sequence of the recombinant polypeptide, one or more recombinase recognition sequences. For example, the recombinase recognition sequences may reside at the 5'- and 3'-end of the respective sequence. The recombinant polypeptide can be a reporter gene in this case, i.e., a gene whose gene product may be easily detected and quantitatively determined. After selection of a stable cell line having a strong expression of the reporter proteins, i.e., of the gene product encoded by the reporter gene, a nucleic acid molecule comprising an expression cassette for another recombinant polypeptide may be integrated into the cell by transfection as a second step. The expression cassette also contains recognition sequences of the same recombination enzyme. After a short-term expression of the recombinase a new production cell line having also a high production efficiency will be generated by the excision of the original and the integration of the recombinant polypeptide newly transfected into the cell. This method reduces the time consuming process of the selection of well expressing production cell lines. Examples for recombinases and respective recognition sequences are: Cre recombinase and loxP recognition sequence from the bacteriophage P1, integrase and attB/attP recognition sequence from the bacteriophage φC31 or Flp recombinase and frt recognition sequence from yeasts (Groth et al., PNAS 97: 5995-6000, 2000; Araki et al., Nucl. Acids Res. 25: 868-872, 1997; O'Gorman et al., Science 251: 1351-1355, 1991). Frequently, not the actual recognition sequences but "pseudo" lox (Araki et al., Nucl. Acids Res. 25: 868-872, 1997) or "pseudo" att (Thyagarajan et al., Mol. Cell. Biol. 21: 3926-3934, 2001) are advantageous for an efficient integration.

The following examples illustrate the invention and are not to be considered limiting. Unless indicated differently, molecular standard methods were used such as described, e.g., by Sambrook et al., 1989, Molecular cloning: A Laboratory Manual, 2. Edition, Cold Spring Harbor Laboratory Press, Cold Spring Harbor, N.Y.

1. Cloning Procedures a) Plasmid pSTK146

Figure 1:
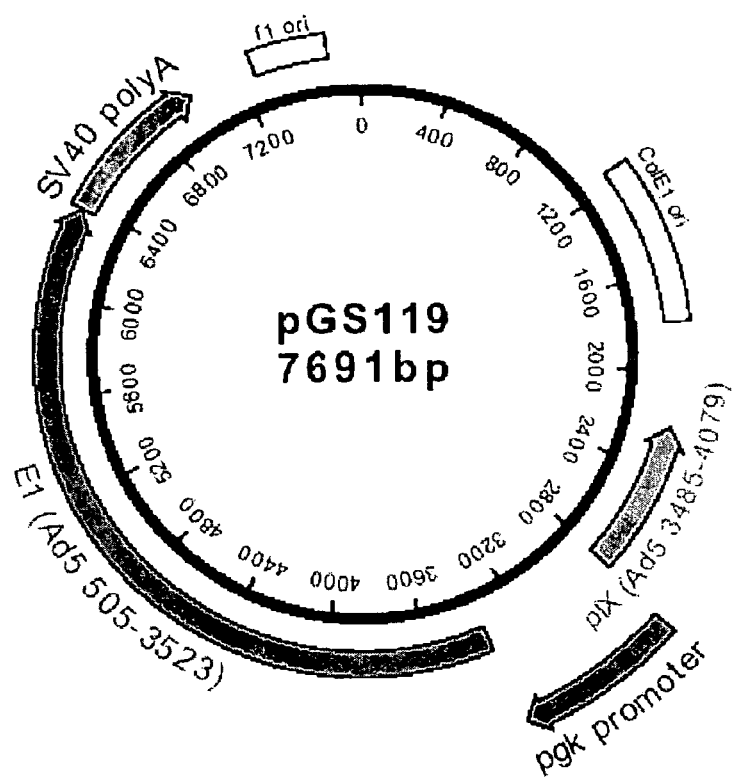
FIG. 1 shows schematically the assembly of plasmid pGS119 for expression of the E1 gene function and of the viral structural protein pIX of adenovirus serotype 5.

Plasmid pSTK146 was described in detail in EP 1 230 354 B1 and comprises the murine phosphoglycerate kinase (pgk) promoter, adenovirus serotype 5 (Ad5) sequences nucleotide (nt.) 505 to 3522 and the splicing and polyadenylation signal of SV40.

b) Plasmid pGS119 (FIG. 1)

Plasmid pGS119 contains the murine pgk promoter, Ad5 sequences nt. 505-3522 containing the entire E1 region, the 3' splicing and polyadenylation signal of SV40 and the pIX region of Ad5 (nt. 3485-4079).

The Ad5 pIX gene sequences are derived from plasmid pXC1 (Microbix Biosystems Inc, Catalogue No. PD-01-03) containing Ad5 sequences nt. 22-5790. Using this plasmid and the primer p9.3485-3504 (CTGGCTCGAGCTCTAGC-GATGAAGATACAG; SEQ ID NO:1) and p9.4079-4060 (GCTGCTCGAGCACTTGCTTGATCCAAATCC; SEQ ID NO:2) Ad5 gene sequences nt. 3485-4079 were amplified by polymerase chain reaction (PCR), cleaved with XhoI (each primer contains one XhoI restriction site) and introduced into the XhoI restriction site of pSTK146.

c) Plasmid pGS122

Plasmid pGS122 contains Ad5 sequences bp 1-4344. In a first step, Ad5 sequences nt. 356-3826 were isolated from pXC1 (Microbix Biosystems Inc, Catalogue No. PD-01-03) using SacII digestion and introduced into the SacII restriction site of pSTK31 (contains a PmeI restriction site followed by Ad5 sequences bp 1-400 in pBluescript). The in such a way generated plasmid pGS120 was linearised with BstEII, and the BstEII fragment from pXC1 containing the Ad5 sequences bp 1914-5185 was introduced (pGS121). Two oligonucleotides Ad5_4297-4344.PX (GCTGGGCGTGGTGCCTAAAAAT-GTCTTTCAGTAGCAAGCTGA TTGCCAGTTTAAAC; SEQ ID NO:3) and Ad5_4344-4297 (TCGAGTTTAAACTGGCAA TCAGCTTGCTACT-GAAAGACATTTTTAGGCACCACGCCCAGCT; SEQ ID NO:4) were hybridised to form the double strand. Plasmid pGS121 was digested with AfeI and XhoI, and the above-mentioned oligonucleotide was introduced. The sequence of the oligonucleotide was selected such that upon introduction into pGS121 the AfeI restriction site at the 5' end is retained, and at the 3' end a PmeI restriction site is followed by the regenerated XhoI restriction site. Thus, the Ad5 sequences in pGS122 are directly flanked by a PmeI restriction site.

d) Plasmid pGS124

Figure 2:
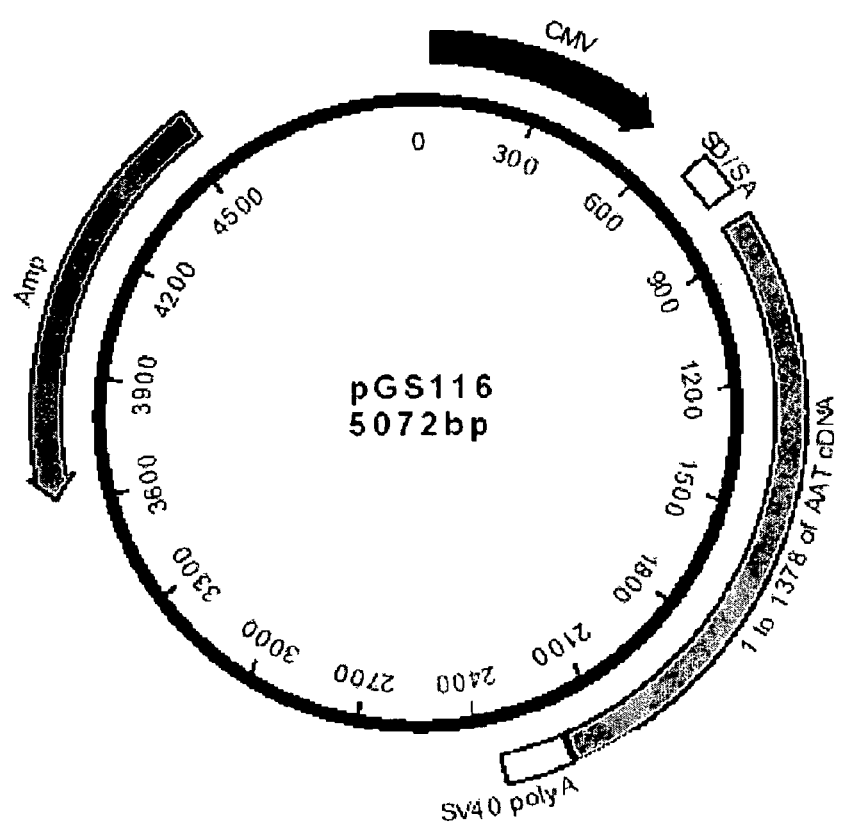
FIG. 2 shows schematically the assembly of plasmid pGS116 for expression of cDNA of the human alpha 1-antitrypsin (hAAT) under the control of the cytomegalovirus (CMV) promoter.

Plasmid pGS124 contains the SV40 promoter and the gene sequence of the SV40 T-antigen. By digestion of SV40 DNA with BamHI and KpnI a 3 kb fragment was cleaved out of the SV40 genome and introduced into pBluescript, digested with BamHI and KpnI. Accordingly, plasmid pGS124 expresses the SV40 T-antigen.

e) Plasmids pGS116 (FIG. 2), pGS129, pGS131, pGS132, pGS133

Plasmids pGS116, pGS129, pGS131, pGS132 and pGS133 express the human alpha 1-antitrypsin (hAAT) under the control of different promoters.

Plasmid pGS116 (FIG. 2) contains the early promoter of the human cytomegalovirus (CMV) followed by a SV40 splice donor/splice acceptor site, the hAAT-cDNA and the SV40 polyadenylation site (polyA). The CMV and SV40 sequences are derived from the plasmid pCMVβ (BD Clontech, Catalogue No. 6177-1). The β galactosidase gene in pCMVβ was deleted by the digestion with NotI and a subsequent fill-in reaction of the 5' overhang and replaced by the hAAT cDNA which was isolated by an EcoRI digestion of the plasmid Ad/PGK-hAAT (Kay et al., Hepatology 21:815-819, 1995).

Plasmid pGS129 contains the above described hAAT cDNA under the control of the human promoters for the elongation factor EF-1α. The CMV promoter was deleted from pGS116 by the digestion of pGS116 with XhoI and EcoRI and a subsequent fill-in reaction of the 5' overhangs and replaced by a 1.3 kb fragment containing the EF-1α promoter.

Plasmid pGS131 contains the hAAT cDNA under the control of a hybrid promoter consisting of the CMV enhancer and the chicken β-actin promoter (CAG promoter). The CMV promoter was replaced by the 1.1 kb CAG promoter by digestion of pGS116 with XhoI and EcoRI and a subsequent fill-in reaction of the 5' overhangs.

Plasmid pGS132 contains the hAAT cDNA under the control of the Rous sarcoma virus (RSV) promoter. The CAG promoter in pGS116 was deleted by a restriction digest with XhoI and EcoRI and subsequent fill-in reaction of the 5' overhangs and replaced by the 0.58 kb RSV promoter.

In plasmid pGS133, the expression of the hAAT cDNA is controlled by the early promoter of Simian virus 40 (SV40). The CMV promoter was deleted from pGS116 by the digestion with XhoI and EcoRI and a subsequent fill-in reaction of the 5' overhangs and replaced by the 0.23 kb SV40 promoter.

f) Plasmid pGS126

Plasmid pGS126 contains the following elements: the E1 expression cassette consisting of pkg promoter, Ad5 sequences nt. 505-3522, SV40 polyA, the pIX expression cassette consisting of Ad5 sequences nt. 3485-4079 and the hAAT expression cassette consisting of CMV promoter hAAT cDNA, SV40 polyA. The hAAT expression cassette was isolated by the digest of pGS116 (see 1 e) with EcoRI and HindIII and a subsequent fill-in reaction and introduced into plasmid pGS119 (see 1 b) upon digestion with BamHI and fill-in reaction of the 5' overhangs. Plasmid pGS126 thus expresses the Ad5 E1 and pIX proteins and hAAT.

g) Plasmid pGS123

Plasmid pGS123 contains, in addition to the hAAT expression cassette a matrix associated region (MAR). This MAR localises within a 2085 bp EcoRI/SpeI fragment from the intron region of the gene locus for the human AAT (GenBank Accesion K02212). This fragment is cloned in pBluescript (pGS58) and was introduced into the EcoRI restriction site after the fill-in reaction of the 5' overhangs of pGS116 (see 1 e).

h) Plasmid pGS127

Plasmid pGS127 contains the CMV promoter, the cDNA for the human erythropoietin (Epo) and the SV40 polyA sequence. The β-galactosidase gene was removed from pCMVβ by means of a NotI digestion and replaced by the Epo cDNA.

2. Verification of the Constructs a) Sequence Analysis

The completeness of all plasmids described above was tested by restriction digest. Furthermore, the correct sequence of the adenovirus fragments in pGS119, pGS122 and pGS126 was confirmed by sequence analysis; no alterations in the sequence as compared to the Ad5 wildtype sequence were found.

b) Expression

The plasmids pGS116, pGS129, pGS131, pGS132, pGS133, pGS123 and pGS126 were transfected into HEK293 cells and the expression and secretion of human alpha 1 antitrypsin (hAAT) into the culture supernatant was detected using ELISA (see chapter 6 b).

The plasmids pGS119 and pGS122 were transfected into HeLa cells and the expression of the E1A proteins was analysed by Western blotting using a monoclonal antibody (see chapter 6a).

The plasmid pGS124 was transfected into HeLa and HEK293 cells and the expression of the T-antigen was detected using Western blotting and a monoclonal antibody (Abcam, Cambridge, UK).

3. Cultivation of Cells a) Cell Lines

The cell culture reagents were obtained, unless indicated differently, from the company Invitrogen GmbH. HEK293 and HeLa cells were cultivated in modified in Eagle's Medium (MEM) with 10% foetal calf serum (FCS), 1× penicillin/streptomycin at 37° C., 95% humidity and 5% $CO_2$.

b) Primary Amniocytes

Primary amniocytes were, following routine methods, obtained during an amniocentesis. 1-2 ml of this amniotic puncture were cultivated with 5 ml Ham's F10 medium, 10% FCS, 2% Ultroser G (CytoGen GmbH), 1× antibiotic/antimycotic at 37° C., 95% humidity and 5% $CO_2$ in 6 cm-Primaria cell culture dishes (Falcon). After 4-6 days the amniocytes started to become adherent, and 3 ml fresh medium plus additives (see above) were added. As soon as the cells were fully adherent, the medium was removed and replaced by 5 ml fresh medium plus additives. For the further passages the confluent cells were washed with PBS, detached with trypsin (TrypleSelect, Invitrogen) and transferred into 10 and 25 ml, respectively, fresh medium plus additives into 10 cm and 15 cm dishes, respectively.

4. Transfection and Transformation of Primary Amniocytes

The primary amniocytes were transfected by the transfection of different combinations of the above described plasmids, the transformed cell lines were isolated and analysed for the expression of the transgene. Subsequently, the generation of hAAT expressing cell lines using the plasmids pGS116 and pGS119 is described in detail. Further cell lines were generated in the same way with the following nucleic acid combinations:

pSTK146 (contains Ad5 sequences nt. 505 to 3522) and pGS116 (contains the CMV-hAAT expression cassette)

pGS119 (contains Ad5 sequences nt. 505 to 4079) and pGS129 (contains the EF-1α hAAT expression cassette)

pGS119 and pGS131 (contains the CAG hAAT expression cassette)

pGS119 and pGS32 (contains the RSV hAAT expression cassette)

pGS119 und pGS133 (contains the SV40 hAAT expression cassette)

pGS119 und pGS123 (contains the CMV hAAT expression cassette and MAR sequences)

pGS122 (contains Ad5 sequences nt. 1 to 4344) and pGS116 (CMV hAAT expression cassette)

pGS126 (contains Ad5 sequences nt. 505 to 4079 and the CMV hAAT expression cassette)

pGS119 and pGS127 (contains the CMV-Epo expression cassette)

pGS124 (expresses T-Ag) and pGS116

For the transfection all plasmids except pGS122 were linearised prior to the transfection by a digest with suitable restriction nucleases. The plasmid pGS122 was digested with PmeI prior to the transfection since the adenovirus sequences in pGS122 are flanked by one PmeI restriction site each. In the case when two plasmids were transfected, 1 µg of each plasmid was used; in the case of a transfection of only one plasmid (pGS126) 2 µg were used. Transformed cell clones could be obtained with all nucleic acid combinations and single clones could be isolated and tested. The number of transformed cell clones was dependent on the used nucleic acid molecule encoding the cell transforming factor. Accordingly, surprisingly and unexpectedly significantly more transformed cell clones were obtained when the plasmid pGS119 was used than when using pSTK146. Furthermore, the transfection with the nucleic acid molecules having E1 as cell transforming factor led to significantly more transformed cell clones than the transfection with nucleic acid molecules expressing the SV40 T-antigen (pGS124). The expression of the recombinant polypeptide was in turn dependent on the promoter used, wherein the use of the SV40 promoter in pGS133 resulted in the lowest expression rates.

Hereinafter, the generation of hAAT expressing cell lines using the plasmid pGS116 and pGS119 is described in detail.

Prior to the transfection, the amniocytes were adapted to Opti-Pro medium with 2% Ultroser. For this purpose, the cells were spiked with fresh Ham's F10 medium (with additives) plus Opti-Pro medium (with 2% Ultroser) in a ratio of 75:25%, 50:50%, 25:75% and 0:100% every 2-3 days.

For the transfection, the cells of an approximately 80° % confluent 15 cm dish were distributed onto 6 cm dishes corresponding to a cell number of $5-7 \times 10^5$ cells per dish. On the following day, the cells on 5 dishes were transfected with 1 µg pGS116 and pGS119, both linearised with ScaI, using the transfection reagent Effectene (Qiagen) according to the manufacturer's protocol. One dish was not transfected and cultivated as a control. On the next day, the cells were washed with PBS, detached with TrypleSelect and transferred to a 15 cm dish. The cells were cultivated for further 10-15 days, wherein the medium was replaced by fresh medium every 3-4 days. During this time the addition of Ultroser was decreased to 1%. After about 10-15 days the cells were confluent and were transferred to 15 cm dishes, as described above.

5. Isolation of the Transformed Cell Clones

A few weeks after the transfection, clonal cell islands could be observed, which were significantly morphologically distinct from the non-transformed amniocytes. These cell islands were picked and transferred onto 24-well-dishes (corresponding to passage 1). The cells were furthermore propagated and transferred to 6 cm dishes at first and later to 15 cm dishes.

Initially, about 40 clones were isolated, which partially were significantly morphologically distinct from each other during the further cultivation. Some of these clones showed a significant "crisis" in the case of a prolonged cultivation, i.e., they were very instable in their growth. The further experiments were limited to the further cultivation and analysis of seven morphologically stable cell clones. These were denoted as follows: 2AI.2, 2AI.3, 2AI.6. 2AI.12, 2AI.15, 2AI.17, 2AI.18.

6. Characterisation of the Cell Lines a) Expression of the E1 Genes (Western Blot)

The expression of the E1A and E1B 21kD proteins was detected in seven clonal cell lines by Western blot analysis using monoclonal antibodies.

Figure 3:
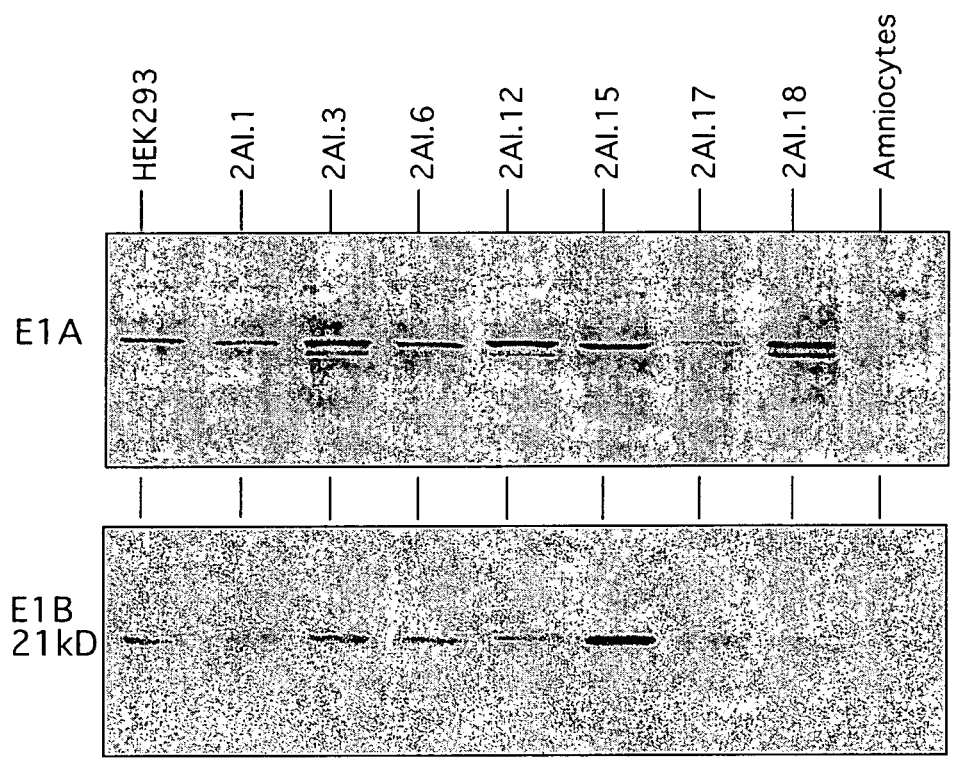
FIG. 3 shows the result of a Western blot in respect to the expression of the E1A and E1B protein of Ad5 in seven different permanent amniocyte based production cell lines for human alpha 1-antitrypsin.

For this purpose, $7 \times 10^5$ cells of each of the individual cell clones were plated in a 6-well-dish each. Seventy-two hours later the cells were detached with Tris-saline/4 mM EDTA, pelleted, resuspended in 100 µl Tris-saline and lysed by the addition of 30 µl 4×SDS-loading buffer (40% glycerol, 1.4 M mercaptoethanol, 8% SDS, 250 mM Tris/HCl pH 7). As a negative control a lysate was used which was prepared from the same number of primary amniocytes. As a positive control served a lysate of HEK293 cells. 10 µl each of these protein mixtures were electrophoretically separated on a 10% SDS polyacrylamide gel and transferred onto a nitrocellulose membrane. The membrane bound proteins were visualised by chemoluminescence (ECL, Amersham) by the incubation with an anti-E1A and anti-E1B 21 kD antibody, respectively, (Oncogene Research) and an HRP-conjugated anti-mouse (E1A, Jackson ImmunoResearch Laboratories) and an anti-rat (E1B 21 kD, Oncogene Research) antibody, respectively, and subsequent incubation. The results of the Western blots with E1A and E1B are depicted in FIG. 3 and show that all examined cell lines express the E1A proteins (3 bands at 30-50 kD) and the E1B 21 kD protein.

b) hAAT-Expression (Western Blot)

The expression of hAAT was detected intracellularly (in the clonal cell lines) and after secretion (in the medium), respectively, also by means of Western Blot analysis using a monoclonal hAAT specific antibody. For this purpose, $7 \times 10^5$ cells of the single cell clones were each plated in a 6-well-dish. As a negative control the same cell of a cell number clone was used which was generated by the transfection of primary amniocytes with pGS119 only. As a positive control in the subsequent assay served 50 ng purified hAAT from human plasma.

Seventy-two hours later the cell culture supernatants were removed, the cells detached with Tris-saline/4 mM EDTA, pelleted, resuspended in 100 µl Tris-saline and lysed by the addition of 30 µl 4×SDS loading buffer. For the detection of the intracellular hAAT 10 µl of the protein mixture of the lysed cells were electrophoretically separated and visualised by means of a monoclonal hAAT antibody (ICN Biomedicals) and a HRP-conjugated anti goat antibody (Pierce) with a subsequent chemoluminescence staining. For the detection of secreted hAAT 10 µl of the cell culture medium were spiked with 2×SDS loading buffer, electrophoretically separated and detected as described above.

FIG. 4A shows the hAAT which was secreted from the cells into the culture supernatant, the intracellular expression of hAAT is depicted in FIG. 4B. The lysate for the intracellular detection of hAAT ist, contrary to the cell culture supernatant, concentrated about 20-fold. This means that hAAT is secreted by the cells very efficiently.

c) Quantity and Stability of the hAAT Expression Over Several Passages (ELISA)

The amount of hAAT secreted into the medium was determined quantitatively using the ELISA (Enzyme-linked Immunosorbent Assay) method. For this purpose, $7 \times 10^5$ cells of the different clonal lines were each plated into a 6-well-dish, and the cell culture supernatants were removed after 72 hours. The amount of hAAT was determined by means of ELISA using polyclonal anti-hAAT antibodies (non conjugated and HRP-conjugated; ICN Biomedicals). As control hAAT was used which was purified from human plasma (ICN Biomedicals). FIG. 5A shows the amount of hAAT per cell, expressed in passage 5 of the individual cell clones. The stability of the expression in selected cell clones over several passages is shown in FIG. 5A. The examined cell lines express between 0.2 and 4 pg hAAT per cell constantly over the time period tested of about 20 passages.

d) Glyco-Analysis of hAAT

Since hAAT is a glycoprotein, the degree of glycosylation of hATT was examined in the individual cell clones. For this purpose, the cell clones were adapted to Opti-Pro medium without Ultroser step by step in advance, which results into to the fact that the cells are not adherent any more but grow in suspension. In order to test if the hAAT secreted into the culture supernatant is glycosylated, a digestion with the enzyme peptide-N-glycosidase F (PNGase F) was performed. This enzyme cleaves off sugar residues which are attached to asparagine residues (N-linked) resulting in a decrease of the molecular weight of the protein. 22.5 µl of the cell culture supernatant of the individual cell clones were spiked with 2.5 µl denaturing buffer (10-fold: 5% SDS, 10% β-mercaptoethanol), and the proteins were denatured for 10 minutes at 100° C. Subsequently, 3.5 µl G7 reaction buffer (10-fold: 500 mM Na-phosphate pH 7.5), 3.5 µl 10% NP-40 and 3 µl PNGase F (New England Biolabs; 500 units/µl) were added to the proteins and incubated for 60 minutes at 37° C.

As controls, in each case, 45 ng purified hAAT from human plasma were denatured in 25 μl Opti-Pro medium as described above and spiked with PNGase F and H₂O, respectively. The changes in the molecular weight of hAAT were subsequently detected as described under 6 b) by means of Western blot analysis using a monoclonal hAAT specific antibody. FIG. 6 shows the changes in the molecular weight after digestion of hAAT, expressed in 4 different cell clones, with PNGase F, and hAAT purified from human plasma, respectively. These experiments clearly show that the hAAT synthesised in the single cell clones is glycosylated.

The invention claimed is:

1. A method for the production of a permanent human cell line comprising:

(a) transfecting isolated primary human cells with a nucleic acid molecule or at least two different nucleic acid molecules, wherein in the case that one nucleic acid molecule is transfected, said nucleic acid molecule comprises a sequence or sequences encoding at least one cell transforming factor and an antibody, and wherein in the case that at least two different nucleic acid molecules are transfected, a first nucleic acid molecule comprises a sequence encoding at least one cell transforming factor, and a second nucleic acid molecule comprises a sequence encoding at least one antibody, wherein transfecting said first and second nucleic acid sequences occurs simultaneously;

(b) selecting said permanent human cell line expressing the antibody, wherein the selection is based on expression of said transforming factor and without any additional exogenous chemical selection.

2. The method according to claim 1, wherein the primary human cells are amniocytes, embryonic retina cells as well as embryonic cells of neuronal origin.

3. The method according to claim 1, wherein the cell transforming factors are T-antigen from SV40, E6 and E7 from HPV or E1A and E1B from human adenoviruses.

4. The method according to claim 3, wherein the sequence for E1A and E1B from human adenoviruses comprises the nucleotides 1 to 4344, 505 to 3522 or the nucleotides 505 to 4079 of the human adenovirus serotype 5.

5. The method according to claim 1, wherein, in case that the cell transforming factors are E6 and E7 from HPV, the sequences for E6 are present on one nucleic acid molecule and the sequences for E7 are present on another distinct nucleic acid molecule, and, in case that the cell transforming factors are E1A and E1B from human adenoviruses, the sequences for E1A are present on one nucleic acid molecule and the sequences for E1B are present on another distinct nucleic acid molecule.

6. The method according to claim 5, wherein sequences for the antibody are present on one of the two nucleic acid molecules for a cell transforming factor.

7. The method according to claim 1, wherein the sequence encoding the cell transforming factor or the antibody comprises a heterologous promoter and/or a heterologeous transcriptional termination element.

8. The method according to claim 7, wherein the promoter is the CMV (cytomegalovirus) promoter, EF-1α promoter, CAG promoter, human or murine pgk promoter, RSV promoter or SV40 promoter, and the transcriptional termination element is the polyadenylation sequences of the SV40 Large T-antigen or of the human G-CSF gene.

9. The method according to claim 1, wherein the sequence encoding the antibody comprises recognition sequences for recombinases, which recognition sequences flank the coding sequence of the antibody or the complete expression cassette of the antibody.

10. The method according to claim 9, wherein the recognition sequences are loxP, attB/attP or Frt sequences.

11. A permanent human cell line obtainable according to a method of claim 1.

* * * * *

```
                        SEQUENCE LISTING

<160> NUMBER OF SEQ ID NOS: 4

<210> SEQ ID NO 1
<211> LENGTH: 30
<212> TYPE: DNA
<213> ORGANISM: artificial sequence
<220> FEATURE:
<223> OTHER INFORMATION: Oligonucleotide primer

<400> SEQUENCE: 1
ctggctcgag ctctagcgat gaagatacag                                    30

<210> SEQ ID NO 2
<211> LENGTH: 30
<212> TYPE: DNA
<213> ORGANISM: artificial sequence
<220> FEATURE:
<223> OTHER INFORMATION: Oligonucleotide primer

<400> SEQUENCE: 2
gctgctcgag cacttgcttg atccaaatcc                                    30

<210> SEQ ID NO 3
<211> LENGTH: 56
<212> TYPE: DNA
<213> ORGANISM: artificial sequence
<220> FEATURE:
<223> OTHER INFORMATION: Oligonucleotide primer

<400> SEQUENCE: 3
gctgggcgtg gtgcctaaaa atgtctttca gtagcaagct gattgccagt ttaaac       56

<210> SEQ ID NO 4
<211> LENGTH: 61
<212> TYPE: DNA
<213> ORGANISM: artificial sequence
<220> FEATURE:
<223> OTHER INFORMATION: Oligonucleotide primer

<400> SEQUENCE: 4
tcgagtttaa actggcaatc agcttgctac tgaaagacat ttttaggcac cacgcccagc   60
t                                                                   61
```